(12) United States Patent
Bannino

(10) Patent No.: US 10,327,831 B2
(45) Date of Patent: Jun. 25, 2019

(54) ELECTROSURGERY APPARATUS, IN PARTICULAR FOR ABLATION OF A TISSUE MASS FROM THE BODY OF A HUMAN OR ANIMAL PATIENT

(71) Applicant: OTECH INDUSTRY S.R.L., Turin (IT)

(72) Inventor: Alberto Bannino, Turin (IT)

(73) Assignee: OTECH INDUSTRY S.R.L., Turin (IT)

( * ) Notice: Subject to any disclaimer, the term of this patent is extended or adjusted under 35 U.S.C. 154(b) by 805 days.

(21) Appl. No.: 14/889,548

(22) PCT Filed: May 8, 2014

(86) PCT No.: PCT/IB2014/061289
§ 371 (c)(1),
(2) Date: Nov. 6, 2015

(87) PCT Pub. No.: WO2014/181279
PCT Pub. Date: Nov. 13, 2014

(65) Prior Publication Data
US 2016/0095645 A1   Apr. 7, 2016

(30) Foreign Application Priority Data
May 8, 2013   (IT) ............... TO2013A0368

(51) Int. Cl.
*A61B 18/14*   (2006.01)
*A61B 18/04*   (2006.01)
(Continued)

(52) U.S. Cl.
CPC ........ *A61B 18/042* (2013.01); *A61B 18/1206* (2013.01); *A61B 18/1402* (2013.01);
(Continued)

(58) Field of Classification Search
CPC .............. A61B 18/042; A61B 18/1206; A61B 18/1402; A61B 2018/1213;
(Continued)

(56) References Cited

U.S. PATENT DOCUMENTS 6,206,878 B1 *   3/2001   Bishop ................ A61B 18/042
219/121.55
2003/0125727 A1   7/2003   Truckai et al.
(Continued)

FOREIGN PATENT DOCUMENTS

WO   WO 2011/055368 A2   5/2011

OTHER PUBLICATIONS

International Search Report for International Patent Application No. PCT/IB2014/061289, dated Oct. 9, 2014.
(Continued)

*Primary Examiner* — Thomas A Giuliani
(74) *Attorney, Agent, or Firm* — Merchant & Gould P.C.

(57) ABSTRACT

An electrosurgical apparatus includes a generator system configured to generate a radio-frequency electric signal, and a handpiece to be gripped by an operator and having an end fitted with an active electrode electrically connected to the generator system. The signal is capable of polarizing the active electrode so as to generate a glow plasma discharge in the atmosphere when the active electrode is in the proximity of the tissue mass, without propagation of electric current through the patient's body (B).

14 Claims, 3 Drawing Sheets

(51) Int. Cl.
*A61B 18/12* (2006.01)
*A61B 18/00* (2006.01)

(52) U.S. Cl.
CPC ............... *A61B 2018/00577* (2013.01); *A61B 2018/00702* (2013.01); *A61B 2018/00726* (2013.01); *A61B 2018/00732* (2013.01); *A61B 2018/00761* (2013.01); *A61B 2018/00898* (2013.01); *A61B 2018/00922* (2013.01); *A61B 2018/00958* (2013.01); *A61B 2018/122* (2013.01); *A61B 2018/144* (2013.01)

(58) Field of Classification Search
CPC .... A61B 2018/122; A61B 2018/00577; A61B 2018/00702; A61B 2018/00898; A61B 2018/00761; A61B 2018/00732; A61B 2018/144; A61B 2018/00726; A61B 2018/00958; A61B 2018/00922; A61B 2018/00583
USPC .......................................... 606/34, 38, 41, 42
See application file for complete search history.

(56) References Cited

U.S. PATENT DOCUMENTS

| | | | |
|---|---|---|---|
| 2006/0189976 A1* | 8/2006 | Karni | A61B 18/042 606/41 |
| 2006/0293649 A1 | 12/2006 | Lorang et al. | |
| 2009/0318918 A1* | 12/2009 | DeCesare | A61B 18/148 606/34 |
| 2011/0319887 A1 | 12/2011 | Keppel | |
| 2012/0029506 A1* | 2/2012 | Johnson | A61B 18/042 606/41 |
| 2012/0083782 A1 | 4/2012 | Stalder et al. | |

OTHER PUBLICATIONS

International Preliminary Report on Patentability for International Patent Application No. PCT/IB2014/061289, dated Aug. 17, 2015.

* cited by examiner

ELECTROSURGERY APPARATUS, IN PARTICULAR FOR ABLATION OF A TISSUE MASS FROM THE BODY OF A HUMAN OR ANIMAL PATIENT

This application is a National Stage Application of International Application No. PCT/IB2014/061289, filed 8 May 2014, which claims benefit of Serial No. TO2013A000368, filed 8 May 2013 in Italy and which applications are incorporated herein by reference. To the extent appropriate, a claim of priority is made to each of the above disclosed applications.

BACKGROUND OF THE INVENTION

The present invention relates to an electrosurgical apparatus, in particular for ablation of a tissue mass from the body of a human or animal patient.

In this field, it is widely known to use electrosurgical apparatus comprising a generator system configured to generate a radio-frequency electric signal, and a handpiece to be gripped by an operator and comprising an end fitted with an active electrode electrically connected to said generator system.

However, apparatus of the above-mentioned kind suffer from a few drawbacks.

US 2006/293649 discloses an apparatus designed, which, in order to perform ablations on a patient's body, requires high polarization power, e.g. up to 300 W. Moreover, said apparatus also needs, in addition to the active electrode, a further electrode (also referred to as return plate) to be laid on the patient's body, thus being invasive towards the latter because the plasma discharge generated between the electrodes causes electric current to flow through the human body. Therefore, this type of apparatus suffers from problems of compatibility with particular typologies of patients, e.g. pacemaker carriers, while also significantly increasing the sensation of pain. Furthermore, said apparatus operates at an average temperature that may even reach 90° C., thus preventing coagulation and promoting cellular necrotization, in particular for soft tissues, e.g. mucosae.

US 2011/319887 describes an apparatus wherein a plasma discharge is produced by ionization of inert gases, and wherein a return plate is used. In addition, said document provides for using an inert gas outlet nozzle manufactured from a special material, such as tungsten.

WO 2011/055368 describes an apparatus specifically conceived for deep cutting by means of plasma discharges. In particular, said apparatus is based upon the adoption of a particular handpiece that comprises two close electrodes adapted to generate the energy required for ionizing the gas flow conveyed near such electrodes.

US 2003/125727 proposes an apparatus that makes combined use of photonic sources (UV light) and inert gases, which is mainly intended for laparoscopy applications.

US 2012/083782 relates to an apparatus that comprises a handpiece having a particular structure and including special carbon cylinders allowing to improve the properties of the plasma discharge. In particular, the action of the active electrode is provided by delivering a saline solution through the end of the handpiece.

It is one object of the present invention to provide an electrosurgical apparatus which can overcome the drawbacks of the prior art.

It is a further object of the present invention to provide an improved and reliable electrosurgical apparatus that can nevertheless be produced in a simple and economical manner.

SUMMARY OF THE INVENTION

According to the present invention, this and other objects are achieved through an electrosurgical apparatus.

It is to be understood that the appended claims are an integral part of the technical teachings provided in the following detailed description of the invention.

According to another aspect of the present invention, a method is provided for ablation of a tissue mass from the body of a human or animal patient, which method comprises the following operating steps:

providing a handpiece comprising an end fitted with an active electrode;

generating a radio-frequency electric signal;

supplying said signal to said active electrode, thereby polarizing it; and moving said handpiece to bring said polarized active electrode near said tissue mass, so as to generate a glow plasma discharge in the atmosphere between said active electrode and said tissue mass, without propagation of electric current through the body of said patient.

BRIEF DESCRIPTION OF THE DRAWINGS

Further features and advantages of the present invention will become apparent from the following detailed description, which is supplied by way of non-limiting example with particular reference to the annexed drawings, wherein.

DETAILED DESCRIPTION OF THE PREFERRED EMBODIMENT(S)

Figure 1:
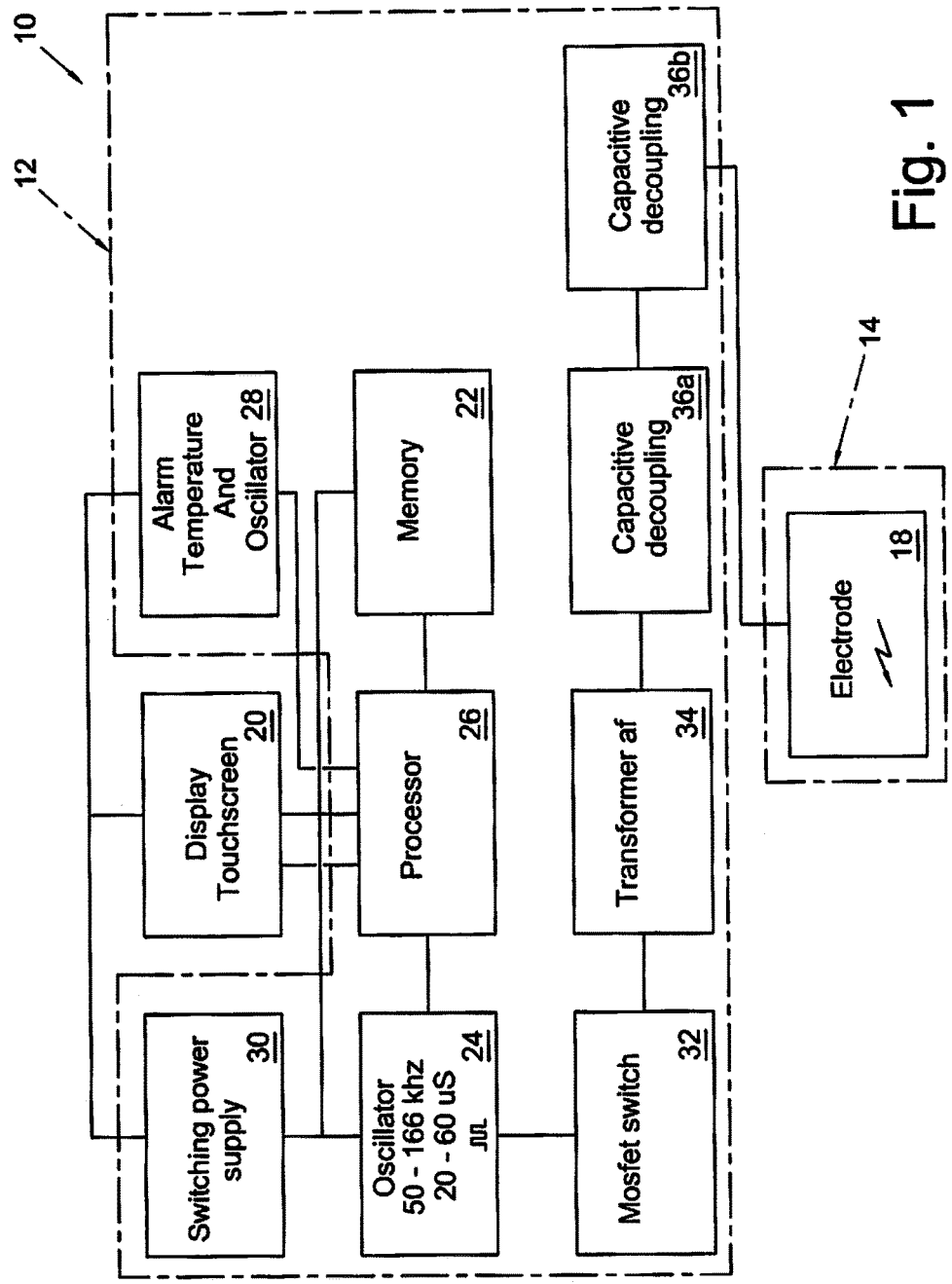
FIG. 1 is a block-diagram representation of an apparatus 10 in accordance with an exemplary embodiment of the present invention.
Figure 2:
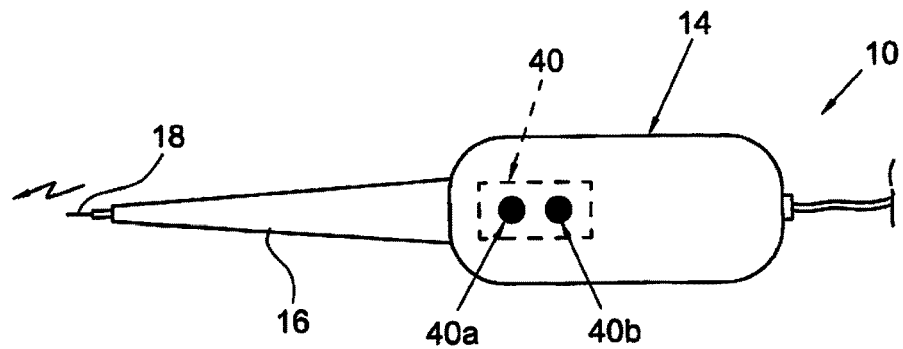
FIG. 2 is a schematic view of a handpiece of the apparatus shown in FIG. 1.
Figure 3:
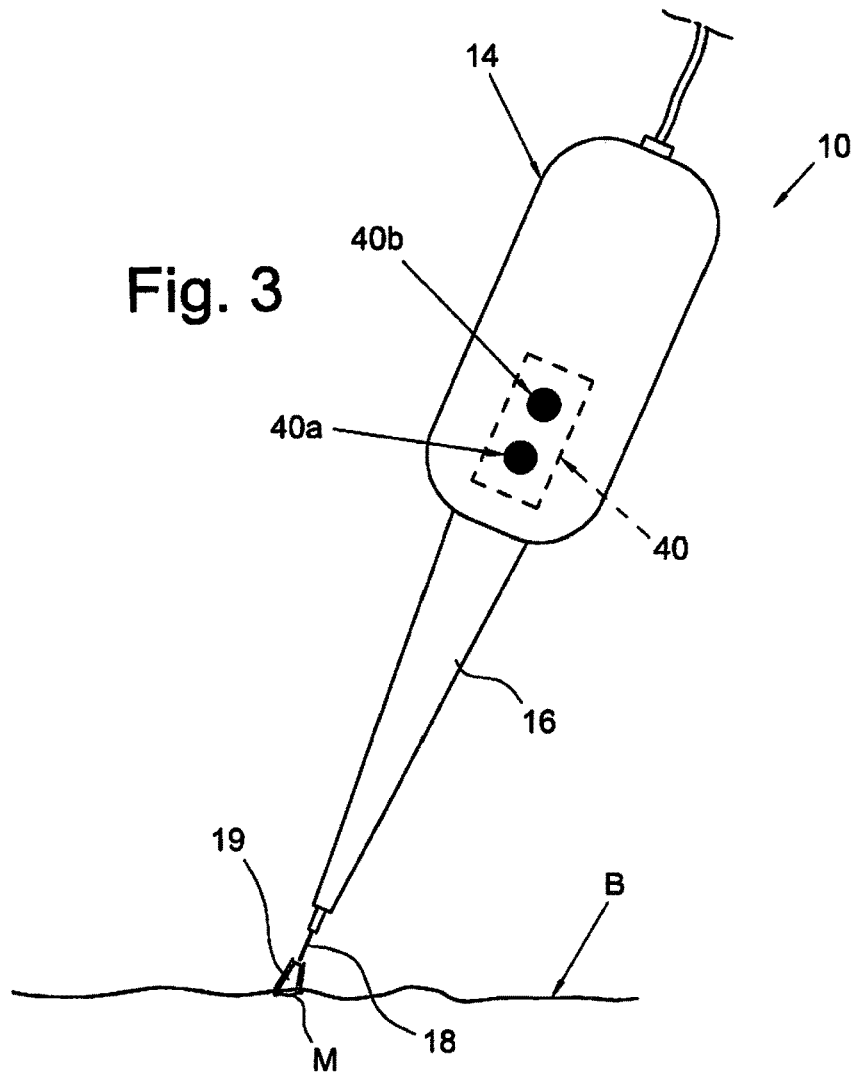
FIG. 3 is a schematic view of the handpiece shown in FIG. 2 in operation.

With reference to the embodiment shown in the drawings, reference numeral 10 designates as a whole an electrosurgical apparatus, in particular for ablation of a tissue mass from the body of a human or animal patient by plasma generation.

Apparatus 10 comprises a generator system 12 configured to generate a radio-frequency electric signal. Apparatus 20 further comprises a handpiece 14 to be gripped by an operator and comprising an end 16 fitted with an active electrode 18 electrically connected to said generator system 12.

Said signal, which is generated by generator system 12, is capable of polarizing active electrode 18, so as to generate a glow plasma discharge 19 in the atmosphere between active electrode 18 and tissue mass M to be subjected to ablation when active electrode 18 is in the proximity of the tissue mass, without propagation of electric current through body B of the patient.

In other words, apparatus 10 provides for ionizing only the atmospheric air between end 16 and the patient's body, by exploiting the potential difference existing between active electrode 18 and the patient's body in order to bring about the dielectric breaking of the insulation bonds of atmospheric air. To achieve this effect, the apparatus does not make use of flows of noble gases emitted through the handpiece, unlike other types of electrosurgical devices that utilize, for example, flows of ionized Argon gas in order to generate a plasma discharge.

Moreover, in such other types of electrosurgical devices electric charges and currents are typically generated which tend to flow through the human body. For this reason, in such other types of devices it is necessary to employ a return electrode or dissipation plate to be applied onto the patient's body, generally on the side opposite to the region where handpiece 14 will be used. According to the present invention, instead, the glow plasma discharge, revealing itself through a visible electric spark, is dispersed thanks to a capability which is peculiar to the patient's body, and therefore it is not necessary to use a return electrode or dissipation plate.

Through the effect of thermal dissipation due to the surrounding atmospheric air, the energy generated by the glow plasma discharge induces, in the tissue mass of the patient's body, a lower temperature (e.g. lower than 60° C., in particular approx. 55° C.) than the other electrosurgical knifes, which normally operate in cutting mode at temperatures in excess of 100° C., thereby typically causing cellular necrotization (with a high risk of producing keloids in the patient's body). Instead, said lower temperature induced by using apparatus 10 is sufficient to obtain vaporization or sublimation of the desired tissue mass, without causing pain and avoiding cell explosion. This allows apparatus 10 to carry out surgical operations on the patient's body even without anaesthesia.

A further advantage is that the low temperature transferred to the tissues makes for an excellent haemostatic effect (coagulation).

Preferably, the electric signal has a frequency between approx. 50 kHz and approx. 166 kHz. In particular, said signal has a duration of the active working cycle (the so-called "duty cycle") comprised between approx. 20 µs and 60 µs.

Preferably, the electric signal has a voltage, measured from a peak (crest or trough) to the next peak (trough or crest), also referred to as "peak-to-peak voltage", of approx. 2000 V.

Preferably, the electric signal supplied to active electrode 18 has a sinusoidal shape.

Preferably, apparatus 10 generates a maximum output current lower than or equal to approx. 0.0005 A.

Preferably, the power output of apparatus 10 is lower than or equal to approx. 1 W.

In the illustrated embodiment, apparatus 10 is adapted to be powered by an electric distribution network, such as a 220 V 50 Hz alternating current mains.

In the illustrated embodiment, the glow plasma discharge is generated when active electrode 18 and tissue mass M are at a distance between approx. 0.5 mm and approx. 2 mm from each other. Advantageously, accidental contact between active electrode 18 and tissue mass M will automatically extinguish the plasma discharge, so that tissues cannot suffer any damage.

Preferably, generator system 12 is protected by an outer casing (not shown) that separates its components from the outside environment.

In the illustrated embodiment, the electric connection between generator system 12 and handpiece 14 is established by means of an electric cable, which allows handpiece 14 to be operated in a remote position or anyway at a distance from generator system 12.

In the illustrated embodiment, apparatus 10 comprises adjustment means 20 (e.g. a device for entering and/or displaying data, such as a touchscreen), programmed for switching generator system 12 among a plurality of preset operating configurations, particularly upon input by an operator wanting to remove a tissue mass from a patient's body. In each one of the operating configurations, the electric signal may assume a respective predefined range of frequency values, and a respective predefined range of duty cycle duration values.

In this manner, it is possible to vary the operating parameters of the device in accordance with the type of surgical operation to be carried out. More specifically, on the one hand, the higher the frequency, the deeper the ablation that will be carried out by apparatus 10; on the other hand, the longer the duty cycle, the higher the energy output. In particular, by increasing the duration of the duty cycle it is possible to ablate solid and compact tissue masses, whereas by reducing said duration, it will only be possible to ablate less resistant and softer tissue masses. In brief, one can set an optimal ablation action by appropriately adjusting the duty cycle duration as a function of the type and compactness of the tissue mass to be removed from the patient's body.

In the illustrated embodiment, generator system 12 can be set into at least one of a plurality of preset operating configurations (specifically defined for the application field of apparatus 10), selected from the group including:

(gynecology, otorhinolaryngology, urology) a predefined range of frequency values comprised between approx. 100 kHz and approx. 166 kHz, and a predefined range of duty cycle duration values comprised between approx. 20 µs and approx. 35 µs;

(dermatology and aesthetic medicine) a predefined range of frequency values comprised between approx. 75 kHz and approx. 120 kHz, and a predefined range of duty cycle duration values comprised between approx. 25 µs and approx. 40 µs;

(dentistry) a predefined range of frequency values comprised between approx. 50 kHz and approx. 150 kHz, and a predefined range of duty cycle duration values comprised between approx. 20 µs and approx. 40 µs; and (implantology and orthopedics) a predefined range of frequency values comprised between approx. 50 kHz and approx. 100 kHz, and a predefined range of duty cycle duration values comprised between approx. 35 µs and approx. 60 µs.

Preferably, adjustment means 20 can further control generator system 12 to vary the frequency assumed by the electric signal within the predefined range of frequency values associated with the operating configuration into which the generator system has been set.

Also preferably, adjustment means 20 can further control generator system 12 to vary the duty cycle duration assumed by the electric signal within the predefined range of duty cycle duration values associated with the operating configuration into which generator system 12 has been set.

In the illustrated embodiment, adjustment means 20 can further control generator system 12 to vary the frequency and the duty cycle duration actually assumed by the electric signal within predefined value ranges associated with the operating configuration into which generator system 12 has been set.

In the illustrated embodiment, generator system 12 comprises a memory 22 storing predefined ranges of frequency and/or duty cycle duration values for each one of said operating configurations.

In the illustrated embodiment, generator system 12 further comprises an oscillator 24 adapted to control the generation of the electric signal for polarizing active electrode 18, particularly in terms of power and duty cycle.

In the illustrated embodiment, generator system 12 further comprises a processor 26 adapted to control oscillator 24, particularly in order to assign appropriate values of frequency and/or duty cycle duration to the electric signal. Preferably, processor 26 is configured to receive, from adjustment means 20, control information indicating the operating configuration selected by the operator and, in particular, suitable for the specific type of surgical operation to be carried out on the patient's body. Furthermore, processor 26 is particularly adapted to control oscillator 24 as a function of said control information received from adjustment means 20.

In the illustrated embodiment, generator system 12 includes acoustic and/or visual warning means 28 adapted to detect and signal any faults relating to the operation of the oscillator and/or to the internal temperature of apparatus 10. Particularly, if adjustment means 20 comprise a touchscreen, warning means 28 may cooperate with the latter to visually signal the faulty condition in a manner perceivable by the operator.

Preferably, generator system 12 can be powered by an external electric power source, such as the electric distribution network, through a switching power supply 30. For example, switching power supply 25 is electrically connected to at least one of adjustment means 20, oscillator 24, processor 26, and warning means 28, so as to supply the power required.

In the illustrated embodiment, between oscillator 24 and active electrode 18, generator system 12 comprises a plurality of output components adapted to supply to active electrode 18 the polarization potential for generating the glow plasma discharge, in particular:

a commutator or switch 32, in particular comprising a semiconductor element (such as a transistor, e.g. a MOSFET), connected downstream of oscillator 24;

a transformer 34, particularly an AF transformer (e.g. with a ferrite core), connected downstream of switch 32; and at least one capacitive decoupling stage, in particular the pair of stages 36a and 36b being connected downstream of AF transformer 34 and upstream of active electrode 18.

In the illustrated embodiment, oscillator 24 is adapted to output a periodic signal, particularly a square-wave signal, to switch 32. Switch 32 then pulses the periodic signal coming from oscillator 24, supplying it to transformer 34. Subsequently, transformer 34 raises the voltage and, by hysteresis effect, causes the signal to become sinusoidal, which is then supplied to the capacitive decoupling stage 36a, 36b, so that the energy is transferred to output electrode 18.

As an alternative to the above, it will be apparent to a man skilled in the art that a different structure may be conceived as concerns said plurality of output components, provided that there is still the possibility of generating and transmitting a periodic signal (e.g. sinusoidal) to at least one final capacitive stage, so that the latter can supply a suitable electric signal to the active electrode.

In the illustrated embodiment, handpiece 12 comprises, on the side opposite to end 16 (which preferably has an elongated and tapered shape), a grip portion 38 to be gripped by the operator for directing electrode 18 near the tissue mass to be subjected to ablation.

Preferably, apparatus 10 is equipped with control means 40 operable by the operator, through which it is possible to control the electric potential output to active electrode 18 from generator system 12. More preferably, control means 40 are located on handpiece 14, e.g. on grip portion 38.

In particular, control means 40 are adapted to selectively stop and allow polarization of active electrode 18 by generator system 12. For this purpose, for example, control means 40 comprise an activation switch 40a (e.g. controllable by means of a push-button, advantageously of the bistable type), adapted to be pressed by the operator in order to start and stop the supply of polarizing potential to active electrode 18. Particularly, at every actuation of activation switch 40a (e.g. via a temporary impulsive pressure exerted on the associated push-button), it alternately switches to, and remains stable in, an activated condition, in which it allows polarization of active electrode 18, and a further deactivated condition, in which said polarization is not allowed. Only by pressing again the activation switch 14a it will be possible to switch again from an activated (or deactivated) condition to the other deactivated (or activated) condition, without the operator having to continually operate the activation switch to keep it in the desired condition.

In the illustrated embodiment, activation switch 40a is located on handpiece 14, e.g. on grip portion 38.

Preferably, control means 40 are adapted to temporarily increase, e.g. double, the flow of electric energy that reaches active electrode 18 from generator system 12 (in particular by increasing the frequency and/or the duty cycle duration beyond the values of the respective ranges assigned thereto in the operating configuration that generator system 12 is currently in), thus creating a so-called "booster" effect. This application is particularly advantageous when the energetic flow of the glow plasma discharge must be quickly adjusted for particular needs that might arise during the surgical operation (e.g. in the event that it should become suddenly necessary to coagulate a capillary or to remove a tissue mass that is more compact and harder than the one currently under operation), without having to change the operating configuration of generator system 12, e.g. through adjustment means 20, or without having to use another separate electrosurgical instrument.

To this end, for example, control means 40 comprise a booster switch 40b (e.g. controllable by means of a push-button, optionally of the monostable type), adapted to be pressed by the operator in order to effect said temporary increase of the supply of polarizing potential to active electrode 18. In the illustrated embodiment, booster switch 40b is located on handpiece 14, e.g. on grip portion 38. In particular, the polarizing power output is increased as long as booster switch 40b remains continually actuated by the operator (e.g. by exerting constant pressure on the associated push-button). When the operator stops actuating it, booster switch 40b will automatically set the polarizing power back to the normal values of the operating configuration assumed by generator system 12.

By way of example, when booster switch 40b is operated, processor 26 will be activated to appropriately control the operating parameters of oscillator 26 in order to obtain the above-mentioned "booster" effect.

Preferably, activation switch 40a and booster switch 40b are arranged side by side.

Figure 4:
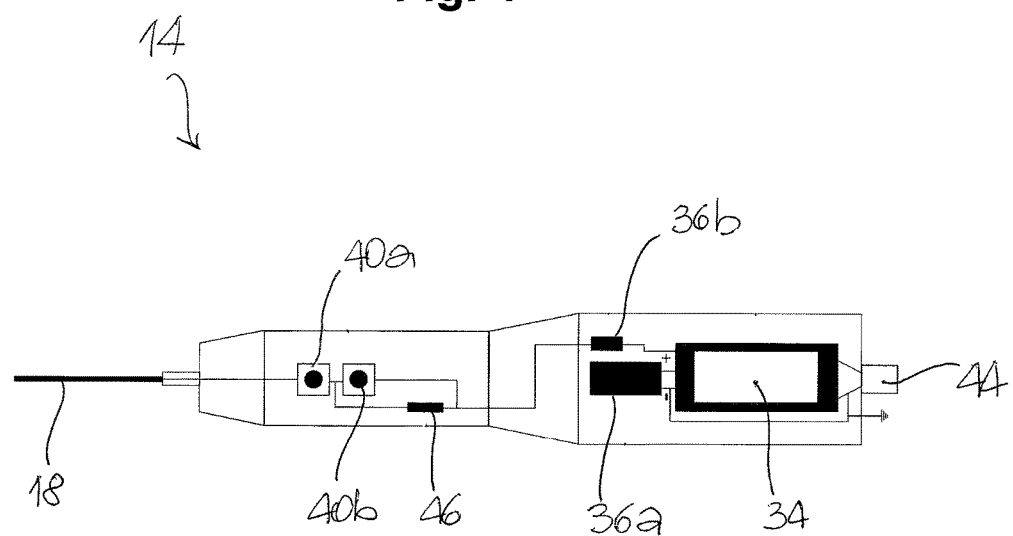
FIG. 4 is a block diagram showing the circuit structure of an exemplary embodiment of the handpiece shown in the preceding figures.

With particular reference to FIG. 4, there is shown a preferred embodiment of handpiece 14 illustrated in the preceding figures. Said handpiece 14 is connected by means of the electric cable coming from system 12, e.g. through a connector 44. Said cable is connected to a transformer 34, which is electrically connected in parallel with a first capacitive stage 36a. There is also a second capacitive stage 36b, which is connected in series to transformer 34 and to the first capacitive stage 36a. In its turn, the second capacitive stage 36b is electrically connected, through at least one activation switch 40a, to active electrode 18. In this manner, when activation switch 40a closes, power will be supplied to active electrode 40a.

Preferably, handpiece 14 comprises a resistor 46 which is electrically connected in series to the second capacitive stage 36b, on one side, and to activation switch 40b, on the other side.

In the illustrated embodiment, handpiece 14 further comprises a booster switch 40b, which is electrically connected in parallel with resistor 46. In this manner, when activation switch 40a and booster switch 40b are closed simultaneously, resistor 46 will be excluded from the path of the electric current coming from system 12, so that the apparatus will be able to operate in "booster" mode.

In the light of the above detailed description, apparatus 10 can operate on both tissues which are good electric conductors, e.g. wet tissues, and tissues which are bad electric conductors, e.g. bone or cartilage.

Moreover, apparatus 10 is suitable for human and veterinary applications, even as concerns excision treatments of skin tumors.

Furthermore, it must be pointed out that the Applicant has found that numerous advantages and benefits can be attained from using the apparatus according to the previously described and illustrated embodiment of the present invention, including:

- substantial absence of pain during the surgical operation;
- fast microcoagulation of the treated region, with low blood loss;
- substantial absence of burns caused by parasitic RF energy;
- negligible or null transfer of electromagnetic fields to the human body;
- negligible or null electric current invasivity;
- better reactivity to post-surgery recovery times by tissue stimulation;
- negligible or no scars nor keloids; and
- practicality for out-patient treatments.

Of course, without prejudice to the principle of the invention, the forms of embodiment and the implementation details may be extensively varied from those described and illustrated herein by way of non-limiting example, without however departing from the scope of the invention.

The invention claimed is:

1. An electrosurgical apparatus for ablation of a tissue mass from the body of a human or animal patient, said apparatus comprising:
    a generator system configured to generate a radio-frequency electric signal, and
    a handpiece configured to be gripped by an operator and comprising an end fitted with a single active electrode electrically connected to said generator system;
    said signal being capable of polarizing said active electrode so as to generate a glow plasma discharge between said active electrode and said tissue mass when said active electrode is in the proximity of said tissue mass;
    wherein power of said electric signal is lower than or equal to 1 W, and said plasma discharge occurs in the atmosphere without propagation of electric current through the body of said patient;
    said generator system is adapted to generate the electric signal having the following parameters:
    a peak-to-peak voltage of 2000 V,
    a maximum output current lower than or equal to 0.0005 A,
    a frequency between 50 kHz and 166 kHz, and
    a duty cycle duration greater than or equal to 20 µs,
    wherein said plasma discharge occurs without returning through said body, said apparatus being provided without a return electrode and configured to prevent conveying an inert gas or a saline solution from said handpiece.

2. An apparatus according claim 1, wherein said generator system further comprises an oscillator for controlling generation of said electric signal for polarizing said active electrode.

3. An apparatus according to claim 1, wherein, between said oscillator and said active electrode, said generator system comprises:
    a commutator or switch connected downstream of an oscillator,
    a transformer connected downstream of said commutator or switch, and
    at least one capacitive decoupling stage electrically connected downstream of said transformer and upstream of said active electrode.

4. An apparatus according to claim 3, wherein said handpiece includes said transformer and said at least one capacitive decoupling stage.

5. An apparatus according to claim 3, wherein said at least one capacitive decoupling stage comprises:
    a first capacitive stage connected in parallel to said transformer;
    a second capacitive stage, on one side electrically connected in series with said transformer and said first capacitive stage, and on another side electrically connected to said active electrode through at least one activation switch.

6. An apparatus according to claim 1, wherein said apparatus comprises an adjustment device for varying the frequency and/or duty cycle duration of said signal upon input by the operator.

7. An apparatus according to claim 6, wherein said adjustment device is programmed to switch said generator system among a plurality of preset operating configurations, wherein in each one of said operating configurations said signal may assume
    a respective predefined interval or range of frequency values, and
    a respective predefined interval or range of duty cycle duration values.

8. An apparatus according to claim 7, wherein said adjustment device is configured to control said generator system to vary at least one of the frequency and the duty cycle duration actually assumed by said electric signal within said predefined value ranges associated with the operating configuration into which said generator system has been set.

9. An apparatus according to claim 1, wherein said glow plasma discharge is generated when said active electrode and said tissue mass are at a distance of 0.5 mm to 2 mm from each other.

10. An apparatus according to claim 1, wherein said signal is adapted to generate the glow plasma discharge which induces a temperature lower than 60° C. in the tissue mass to be subjected to ablation.

11. An apparatus according to claim 1, further comprising a controller operable by the operator, for controlling the electric potential output to said active electrode from said generator system; said controller being located on said handpiece.

12. An apparatus according to claim 11, wherein said controller is adapted to carry out at least one of the following operations:
selectively stopping and allowing polarization of said active electrode by said generator system; and
temporarily increasing flow of electric energy supplied to said active electrode by said generator system.

13. An apparatus according to claim 12, wherein said apparatus comprises an adjustment device for varying the frequency and/or duty cycle duration of said signal upon input by the operator;
wherein said adjustment device is programmed to switch said generator system among a plurality of preset operating configurations, wherein in each one of said operating configurations said signal may assume:
a respective predefined interval or range of frequency values; and
a respective predefined interval or range of duty cycle duration values;
wherein said controller is adapted to temporarily increase said flow of electric energy by increasing at least one of the frequency and the duty cycle duration beyond the values of the respective ranges associated with said operating configuration assumed by said generator system.

14. An electrosurgical apparatus for ablation of a tissue mass from the body of a human or animal patient, said apparatus comprising:
a generator system configured to generate a radio-frequency electric signal, and
a handpiece configured to be gripped by an operator and comprising an end fitted with a single active electrode electrically connected to said generator system;
said signal being capable of polarizing said active electrode so as to generate a glow plasma discharge between said active electrode and said tissue mass when said active electrode is in the proximity of said tissue mass;
wherein power of said electric signal is lower than or equal to 1 W, and said plasma discharge occurs in the atmosphere without propagation of electric current through the body of said patient;
said generator system is adapted to generate the electric signal having the following parameters:
a peak-to-peak voltage of 2000 V,
a maximum output current lower than or equal to 0.0005 A, and
a frequency between 50 kHz and 166 kHz,
wherein said plasma discharge occurs without returning through said body, said apparatus being provided without a return electrode and configured to prevent conveying an inert gas or a saline solution from said handpiece.

* * * * *